United States Patent [19] [11] Patent Number: 4,861,707
Ivanoff et al. [45] Date of Patent: Aug. 29, 1989

[54] HUMAN IMMUNODEFICIENCY VIRUS ANTIGEN

[75] Inventors: Lucinda A. Ivanoff, Springfield, Pa.; Steven R. Petteway, Hockessin, Del.

[73] Assignee: E. I. Du Pont de Nemours and Company, Wilmington, Del.

[21] Appl. No.: 10,056

[22] Filed: Feb. 2, 1987

[51] Int. Cl.[4] .................. C12Q 1/70; C07K 15/04; C07K 15/14; G01N 33/569

[52] U.S. Cl. .................................. 435/5; 422/61; 435/7; 530/350; 530/395; 530/825; 530/826; 436/808; 436/811

[58] Field of Search ............... 435/517; 530/395, 826, 530/350, 825; 422/61; 436/808, 811

[56] References Cited

U.S. PATENT DOCUMENTS

| 4,629,783 | 12/1986 | Cosand | 530/324 |
|---|---|---|---|
| 4,661,445 | 4/1987 | Saxinger et al. | 435/7 |
| 4,692,403 | 9/1987 | Linder et al. | 435/5 |
| 4,708,818 | 11/1987 | Montagnier et al. | 435/5 |
| 4,716,102 | 12/1987 | Levy | 435/5 |
| 4,753,873 | 6/1988 | Beltz et al. | 435/5 |

FOREIGN PATENT DOCUMENTS

| 0185444 | 10/1985 | European Pat. Off. |
|---|---|---|
| 0199301 | 10/1986 | European Pat. Off. ........... 435/5 |
| 0227169 | 12/1986 | European Pat. Off. |
| 86/01535 | 8/1985 | World Int. Prop. O. |

OTHER PUBLICATIONS

Palker et al., "A Conserved Region at the COOH Terminus of Human Immunodeficiency Virus gp120 Envelope Protein Contains an Immunodominant Epitope", Proc. Natl. Acad. Sci., U.S.A., 84, (Apr. 1987), 2479–2483.
Chang et al., "Detection of Antibodies to Human T--Cell Lymphotropic Virus III (HTLV-III) with and Immunoassay Employing a Recombinant *Escherichia Coli*-Derived Viral Antigenic Peptide", Bio/Technology, 3, (Oct. 1985):905–908.
Pauletti et al., "Application of a Modified Computer Algorithm in Determining Potential Antigenic Determinants Associated with the AIDS Virus Glycoprotein", Analytical Biochemistry, 151, (Dec. 1985): 540–546.
Montagnier et al., "Identification and Antigenicity of the Major Envelope Glycoprotein of Lymphadenopathy-Associated Virus", Virology, 144, (1985):283–289.
Barin et al., "Virus Envelope Protein of HTLV-III Represents Major Target Antigen for Antibodies in AIDS Patients", Science, 228, (May 31, 1985):1094–1096.
Robey et al., "Characterization of Envelope and Core Structural Gene Products of HTLV-III with Sera from AIDS Patients", Science, 228, (May 3, 1985):593–595.
Veronese et al., "Characterization of gp41 As the Transmembrane Protein Coded by the HTLV-III/-LAV Envelope Gene", Science, 229, (Sep. 27, 1985):1402–1405.
L. Ratner, et al., Nature, vol. 313, No. 6000, pp. 277–284, 1/24/85, "Complete Nucleotide Sequence of the AIDS Virus, HTLV-III."
S. D. Putney et al., Science, vol. 234, pp. 1392–1395, 12/86, "HTLV-III/LAV-Neutralizing Antibodies to an *E. coli*-Produced Fragment of the Virus Envelope."
B. R. Starcich et al., Cell, vol. 45, pp. 637–648, 6/86, "Identification and Characterization of Conserved and Variable Regions in the Envelope Gene of HTLV-III/-LAV, the Retrovirus of AIDS."
N. W. Tietz et al., Fundamentals of Clinical Chemistry, p. 101.

(List continued on next page.)

Primary Examiner—Christine M. Nucker

[57] ABSTRACT

A recombinant peptide displaying the antigenicity of Human Immunodeficiency Virus (HIV) viral antigens is disclosed. The peptide comprises an antigenic segment having about 150 to about 400 amino acids corresponding to at least about 30 amino acids of the C-terminal of the gp120 domain and at least about 120 amino acids of the N-terminal of the gp41 domain.

9 Claims, 6 Drawing Sheets

```
           BglII
GAGATCTTCAGACCTGGAGGAGGAGATATGAGGGACAATTGGAGAAGTGAATTATATAAATATAAAGTAGTAAAA
GluIlePheArgProGlyGlyGlyAspMetArgAspAsnTrpArgSerGluLeuTyrLysTyrLysValValLys
  ⇧
  ◆

ATTGAACCATTAGGAGTAGCACCCACCAAGGCAAAGAGAAGAGTGGTGCAGAGAGAAAAAAGAGCAGTGGGAATA
IleGluProLeuGlyValAlaProThrLysAlaLysArgArgValValGlnArgGluLysArgAlaValGlyIle

GGAGCTTTGTTCCTTGGGTTCTTGGGAGCAGCAGGAAGCACTATGGGCGCAGCGTCAATGACGCTGACGGTACAG
GlyAlaLeuPheLeuGlyPheLeuGlyAlaAlaGlySerThrMetGlyAlaAlaSerMetThrLeuThrValGln

GCCAGACAATTATTGTCTGGTATAGTGCAGCAGCAGAACAATTTGCTGAGGGCTATTGAGGCGCAACAGCATCTG
AlaArgGlnLeuLeuSerGlyIleValGlnGlnGlnAsnAsnLeuLeuArgAlaIleGluAlaGlnGlnHisLeu

TTGCAACTCACAGTCTGGGGCATCAAGCAGCTCCAGGCAAGAATCCTGGCTGTGGAAAGATACCTAAAGGATCAA
LeuGlnLeuThrValTrpGlyIleLysGlnLeuGlnAlaArgIleLeuAlaValGluArgTyrLeuLysAspGln

CAGCTCCTGGGGATTTGGGGTTGCTCTGGAAAACTCATTTGCACCACTGCTGTGCCTTGGAATGCTAGTTGGAGT
GlnLeuLeuGlyIleTrpGlyCysSerGlyLysLeuIleCysThrThrAlaValProTrpAsnAlaSerTrpSer
```

OTHER PUBLICATIONS

S. Modrow et al., *J. of Virology*, vol. 61, No. 2, pp. 570-578, 2/87, "Computer-Assisted Analysis of Envelope Protein Sequences of Seven Human Immunodeficiency Virus Isolates: Predication of Antigenic Epitopes in Conserved and Variable Regions".

R. Crowl et al., *Cell*, vol. 41, pp. 979-986, 7/85, "HTLV-III *env* in *E. coli* are Recognized by Antibodies Present in the Sera of AIDS Patients".

P. N. Lelie et al., IV Int'l AIDS Symposium, Stockholm, 1988, Earlier Detection of HIV-Infection Using Second-Generation Anti-HIV Assays, Poster, 1069.

F. Spielberg et al., Comparative Evaluation of Rapid, Visually Read HIV Antibody Screen Assays at Mama Yemo Hospital, Kinshasa, Zaire, 10/28/88.

D. Stipp, *The Wall Street Journal*, 6/21/88, p. 14, "Cambridge BioScience Blocked Group from Publishing Data on AIDS Test".

R. Tritch et al., 1986 UCLA Symposia, "Expression of HTLVIII GAG and Envelope Proteins in *E. coli*: Reaction with AIDS Sera."

D. Reed et al., 1986 UCLA Symposia, "Immunological Characterization of HTLVIII Recombinant Proteins Potential as Diagnostics or Vaccines."

S. R. Petteway, Jr. et al., *Viruses and Human Cancer*, pp. 15-28, 1987, "Immunological Characterization of the HTLV-III Recombinant Proteins: Potential as Diagnostics and Vaccine Candidates."

NUCLEOTIDE BASE SEQUENCE NUMBERS

FIG. 2

```
BglII
GAGATCTTCAGACCTGGAGGAGGAGATATGAGGAGGACAATTGGAGAAGTGAATTATATAAATATAAAGTAGTAAAA
GluIlePheArgProGlyGlyGlyAspMetArgArgThrIleGlyGluValAsnTyrIleAsnIleLysValValLys
```
```
ATTGAACCATTAGGAGTAGCACCCACCAAGGCAAAGAGAAGAGTGGTGCAGAGAGAAAAAGAGCAGTGGGAATA
IleGluProLeuGlyValAlaProThrLysAlaLysArgArgValValGlnArgValLysArgGluLysGluGlnTrpGlyIle GGAGCTTTGTTCCTTGGGTTCTTGGAGCAGCAGGAAGCACTATGGGCGCAGCGTCAATGACGCTGACGGTACAG
GlyAlaLeuPheLeuGlyPheLeuGlyAlaAlaGlySerThrMetGlyAlaAlaSerThrThrLeuThrValGln GCCAGACAATTATTGTCTGGTATAGTGCAGCAGCAGAACAATTGCTGAGGGCTATTGAGGCGCAACAGCATCTG
AlaArgGlnLeuLeuSerGlyIleValGlnGlnGlnAsnAsnLeuLeuArgAlaIleGluAlaGlnGlnHisLeu TTGCAACTCACAGTCTGGGGCATCAAGCAGCTCCAGGCAAGAATCCTGGCTGTGGAAAGATACCTAAAGGATCAA
LeuGlnLeuThrValTrpGlyIleLysGlnLeuGlnAlaArgIleLeuAlaValGluArgTyrLeuLysAspGln CAGCTCCTGGGGATTTGGGGTTGCTCTGGAAAACTCATTTGCACCACTGCTGTGCCTTGAATGCTAGTTGGAGT
GlnLeuLeuGlyIleTrpGlyCysSerGlyLysLeuIleCysThrThrAlaValProTrpAsnAlaSerTrpSer
```

```
                                                                    HindIII
AATAAATCTCTGGAACACATTGGAATAATAACATGACCTGGATGGAGTGGGACAGAGAAATTAACAATTACACAAGC
AsnLysSerLeuGluGlnIleTrpAsnAsnMetThrTrpMetGluTrpAspArgGluIleAsnAsnTyrThrSer ←

TTAATACACTCCTTAATTGAAGAATCGCAAAACCAGCAAGAAAAGAATTGAACAAGAATTATTGGAATTAGATAAA
LeuIleHisSerLeuIleGluGluSerGlnAsnGlnGluLysAsnGluGlnLeuLeuLeuGluLeuAspLys

TGGGCAAGTTTGTGTGGAATTGGTTTAACATAACAAATTGGCTGTGGTATATAAAATTATTCATAATGATAGTAGGA
TrpAlaSerLeuTrpAsnTrpPheAsnIleThrAsnTrpLeuTrpTyrIleLysLeuPheIleMetIleValGly

GGCTTGGTAGGTTTAAGAATAGTTTTTGCTGTACTTTTCTGTAGTGAATAGAGTTAGGCAGGATATTCACCATTA
GlyLeuValGlyLeuArgIleValPheAlaValLeuSerValValAlaSerArgValAlaArgGlnGlyTyrSerProLeu

TCGTTTCAGACCCACCTCCCAATCCCGAGGGGACCCGACAGGCCCGAAGGAATAGAAGAAGAAGGTGGAGAGAGA
SerPheGlnThrHisLeuProIleProArgGlyProArgGlyProGluGlyIleGluGluGluGluGlyGlyGluArg

BamHI
GACAGAGACAGATCCATTCGATTAGTGAACGGATCC
AspArgAspArgSerIleArgLeuValAsnGlySer ⇦
```

```
ATGGGGCCAGGGTTC
MetGlyProGlyPhe

GATTACGCAGTGGCTATGGCTAAAAGAAACATTGTTACAGCAACTACTAGCAAGGGAGAGTTCACTACTATGTTAGGA
AspTyrAlaValAlaMetAlaLysArgAsnIleValThrAlaThrThrSerLysGlyGluPheThrMetLeuGly

GTCCACGACAACGTGGCTATTTTACCAACCCACGCTTCACCTGGTGAAAGCATTGTGATCGATGGCAAAGAAGTG
ValHisAspAsnValAlaIleLeuProThrHisAlaSerProGlyGluSerIleValIleAspGlyLysGluVal

BglII
GAGATCTTCAGACCTGGAGGAGAGATATGAGGGACAATTGGAGAAGTGAATTATATAAATATAAGTAGTAAAA
GluIlePheArgProGlyGlyGlyAspMetArgArgAspAsnTrpArgSerGluLeuTyrLysTyrLysValValLys

ATTGAACCATTAGGAGTAGCACCCAAGGCAAAGAGAAGAGTGGTGCAGAGAGAAAAAGAGCAGTGGAATA
IleGluProLeuGlyValAlaProThrLysAlaLysArgArgValValGlnArgGluLysArgAlaValGlyIle

GGAGCTTTGTTCCTTGGGTTCTTGGGAGCAGGAAGCACTATGGGCGCAGGTCAATGACGCTGACGGTACAG
GlyAlaLeuPheLeuGlyPheLeuGlyAlaAlaAlaGlySerThrMetGlyAlaAlaSerMetThrLeuThrValGln

GCCAGACAATTATTGTCTGGTATAGTGCAGCAGCAGAACAATTGCTGAGGCTATTGAGGCGCAACAGCATCTG
AlaArgGlnLeuLeuSerGlyIleValGlnGlnGlnAsnAsnLeuLeuArgAlaIleGluAlaGlnGlnHisLeu

TTGCAACTCACAGTCTGGGCATCAAGCAGCTCCAGGCAAGAATCCTGGCTGTGGAAAGATACCTAAAGGATCAA
LeuGlnLeuThrValTrpGlyIleLysGlnLeuGlnAlaArgIleLeuAlaValGluArgTyrLeuLysAspGln
```

```
CAGCTCCTCGGGATTTGGGGTTGCTCTCTGGAAAACTCATTTGCACCACTGCTGTGCCTTGGAATGCTAGTTGGAGT
GlnLeuLeuGlyIleTrpGlyCysSerGlyLysLeuIleCysThrThrAlaValProTrpAsnAlaSerTrpSer
                                                                    HindIII
AATAAATCTCTGAACACATTTGGAATAACATGACCTGGATGGAGTGGGACAGAGAAATTAACAATTACACAAGC
AsnLysSerLeuGluHisIleTrpAsnAsnMetThrTrpMetGluTrpAspArgGluIleAsnAsnTyrThrSer TTAATACACTCCTTAATTGAAGAATCGCAAAACCAGCAAGAAAAGAATGAACAAGAATTATTGGAATTAGATAAA
LeuIleHisSerLeuIleGluGluSerGlnAsnGlnGlnGluLysAsnGluGlnGluLeuLeuGluLeuAspLys TGGGCAAGTTTGTGGAATTGGTTTAACATAACAAATTGGCTCTGTGGTATATAAAATTATTCATAATGATAGTAGGA
TrpAlaSerLeuTrpAsnTrpPheAsnIleThrAsnTrpLeuTrpTyrIleLysLeuPheIleMetIleValGly GGCTTGGTAGGTTTAAGAATAGTTTTTGCTGTACTTTCTGTAGTGAATAGAGTTAGGCAGGATATTCACCATTA
GlyLeuValGlyLeuArgIleValPheAlaValLeuSerValValAlaAsnArgValArgGlnTyrSerProLeu TCGTTTCAGACCCACCTCCCAATCCCGAGGGGACCCCGACAGGCCCGAAGGAATAGAAGAAGAAGGTGGAGAGAGA
SerPheGlnThrHisLeuProIleProArgGlyProAspArgProGluGlyIleGluGluGluGluGlyGluArg BamHI
GACAGAGACAGATCCATTCGATTAGTGAACGGATCC
AspArgAspArgSerIleArgLeuValAlaAsnGlySer
```

FIG. 4 (Continued)

HUMAN IMMUNODEFICIENCY VIRUS ANTIGEN

BACKGROUND OF THE INVENTION

1. Field of the Invention

The present invention concerns antigens and vaccines for infectious diseases and, more particularly, to antigens useful in the diagnosis and treatment of Human Immunodeficiency Virus.

2. Background of the Invention

Human Immunodeficiency Virus (HIV, also HTLV-III, LAV, ARV), a cytopathic lymphotropic retrovirus, is considered the probable causative agent of Acquired Immunodeficiency Syndrome (AIDS) in humans. [Gallo, et al., *Science,* 224:500 (1984); Popovic, et al., *Science,* 224:497 (1984); Sarngadharan, et al., *Science,* 224:506 (1984)]. The underlying disease state involves a tropism of HIV for the T4+lymphocyte subset resulting in a selective depletion of the helper/inducer cells of the immune system, leaving the individual defenseless against a number of opportunistic infections.

There are currently more than 27,700 diagnosed cases of AIDS in the United States and the U.S. Public Health Service predicts that by the end of 1991 more than 179,000 persons will have the disease. It is believed that only 10 to 15 percent of those with clinical symptoms and 1 to 2 percent of those infected with HIV suffer the clinical syndrome of AIDS. The development of diagnostics and vaccines to HIV is the subject of intense medical research.

The nucleotide sequence of several independent viral isolates of HIV have been determined. [Ratner et al., *Nature,* 313(6000):227 (1985)]. The viral genome is reported to contain about 10 kilobases which encode four long open reading frames- gag, pol, sor, and env. The env open-reading frame of HIV, which consists of 863 amino acids, has been reported to encode a 160 kd precursor glycoprotein, designated gp160. This precursor glycoprotein is thought to be processed into a 120 kd exterior glycoprotein, designated gp120, and a 41 kd transmembrane protein, designated gp41. All three proteins have been found to react with AIDS patient sera. [Barin et al., *Science,* 228:1094 (1985); Sarngadharan et al., *Science,* 224:506 (1984)]Recombinant proteins derived from the env reading frame and other regions of the HIV genome are being studied as diagnostic and vaccine candidates. The following references are representative of this ongoing research.

Chang et al., *Science,* 228:93 (1985) discloses the expression in *E. coli* of open reading frame gene segments of HTLV-III. Cloned HTLV-III DNA was sheared into approximately 500-base-pair fragments and inserted into an "open reading frame" expression vector. The inserted DNA was expressed in *E. coli* transformants as fusion proteins which were immunoreactive with AIDS serum. Reactive fragments were derived from the open reading frame DNA segments corresponding to the gag and pol coding regions and also the open reading frame region env-lor located near the 3' end of the viral genome.

Crowl et al., *Cell,* 41:979 (1985) discloses HTLV-III env gene products synthesized in *E. coli* which are recognized by antibodies present in the sera of AIDS patients. A large segment of the env gene (1800 bp) was inserted into an expression vector. The inserted DNA was expressed in *E. coli* transformants as a recombinant protein containing 611 amino acids which encompassed both the extracellular and the membrane associated regions of the native protein. AIDS patient sera recognized the bacterially synthesized envelope protein in Western blot experiments.

Chang et al., *Nature,* 315:151 (1985) reports the production of a recombinant 15K peptide encoded by the 3' end of the viral pol gene. The peptide is described as strongly immunoreactive with with anti-HTLV-III antibodies present in sera from AIDS patients. Allan et al., *Science,* 230:810 (1985) discloses a HTLV-III/LAV 27,000 MW protein having a coding origin 3' to the env gene.

U.S. Pat. No. 4,520,113, issued to Gallo et al., discloses serological detection of antibodies to, HTLV-III in sera of patients with AIDS and pre-AIDS conditions. HTLV-III isolated from AIDS patients and transmitted by cocultivation with an HT cell line is detected by antibodies from human sera taken from AIDS patients. The most prominant reactions are said to be directed to gp41, a 41,000 MW protein constituting the envelope antigen of the HTLV-III virus.

SUMMARY OF THE INVENTION

The invention provides a recombinant peptide displaying the antigenicity of Human Immunodeficiency Virus (HIV) viral antigens. The peptide comprises an antigenic segment having about 150 to about 400 amino acids corresponding to at least about 30 amino acids of the C-terminal of the gp120 domain and at least about 120 amino acids of the N-terminal of the gp41 domain.

BRIEF DESCRIPTION OF THE DRAWINGS

FIG. 2 is a schematic illustration of nucleotide sequences which correspond to those encoding preferred antigenic segments. These sequences are reproduced from Ratner et al. The BglII to BamH1 nucleotide sequence of HIV is shown by open arrows and the BglII to HindIII nucleotide sequence of HIV is shown by solid arrows. The derived amino acid sequences which correspond to those of the antigenic segments are shown below the nucleotide sequences.

FIG. 4 is a schematic illustration of a nucleotide sequence which corresponds to that encoding ENV9. This peptide has about 340 amino acids which correspond to about 54 amino acids from the N-terminal of the poliovirus sequence of pEXC, about 46 amino acids of the C-terminal of the gp120 domain and about 240 amino acids of the N-terminal of the gp41 domain. The derived amino acid sequence which corresponds to that of ENV9 is shown below the nucleotide sequence.

DETAILED DESCRIPTION OF THE INVENTION

Figure 1:
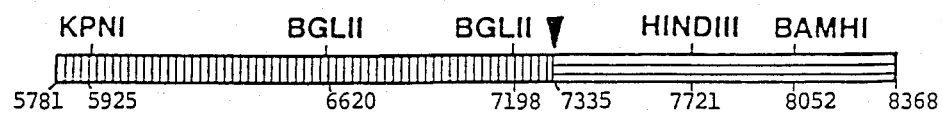
FIG. 1 is a restriction endonuclease map of the gp120 and gp41 domains of HIV. The nucleotide base sequence numbers shown below the map correspond to those shown in the nucleotide sequence published in Ratner et al., *Nature,* 313(6000):227 (1985) (hereinafter *Ratner et al.*), the disclosure of which is incorporated herein by reference.
Figure 3:
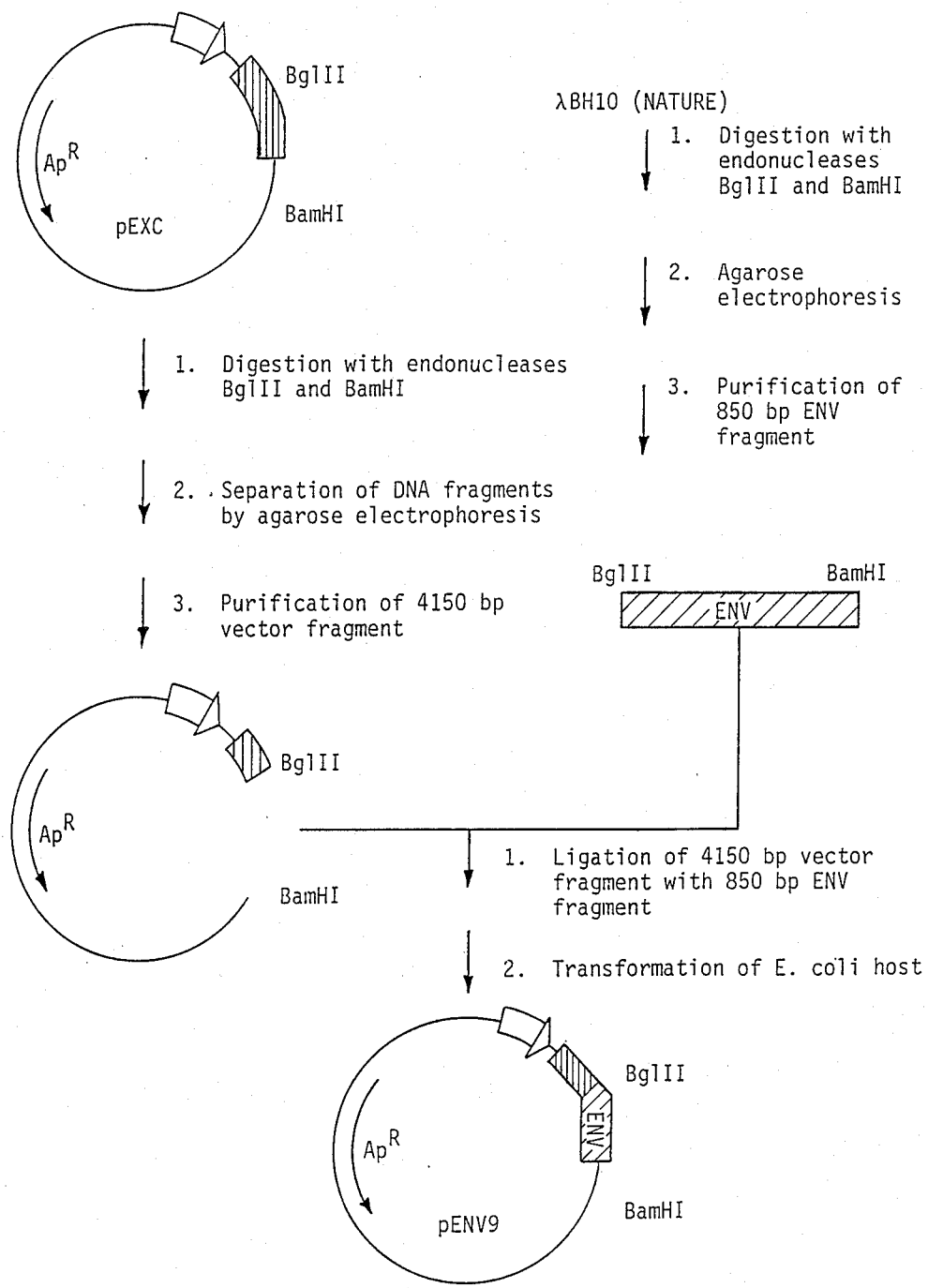
FIG. 3 is a flow diagram illustrating construction of plasmid pENV9 described in Example 1.

A recombinant peptide having residues from both the gp120 and gp41 domains of HIV has been created which is highly immunoreactive with the sera of HIV infected individuals. The term "peptide" is well known in the art and refers to a compound of two or more amino acids joined by a peptide bond. The peptide of the invention comprises a antigenic segment having about 150 to about 400 amino acids corresponding to at least about 30 amino acids of the C-terminal of the gp120 domain and at least about 120 amino acids of the N-terminal of the gp41 domain. The specified domains of HIV are known in the art.

It is to be understood that the expression "corresponding to" includes modifications of the specified amino acid sequences which do not adversely affect the antigenic characteristics of the peptide of the invention. In addition to the antigenic segment defined above, the peptide can contain additional amino acids corresponding to other domains of HIV or other sources, such as a plasmid. One skilled in the art could align the amino acid sequences of peptides from different sources to the schematic of FIG. 2 or the nucleotide sequence of Ratner et al. to identify the segments therein which correspond to the peptide defined herein.

Since HIV infection leads to a series of clinical manifestations accompanied by variable antibody levels to different antigens, useful blood screening/diagnostic reagents should contain multiple antigens. Seroepidemiological studies indicate that the major antigens from gp120 and gp41 are necessary for broad sensitivity to serum antibodies. The antigenic segment of the peptide of the invention contains at least two conserved antigens from the HIV envelope protein. One antigen is an early detection antigen derived from the gp120 domain and the other is a highly reactive antigen from the gp41 domain. For this and other reasons, the peptide of the invention provides a sensitive diagnostic reagent for detecting HIV infection.

The sensitivity of the peptide permits the detection of HIV infection using smaller amounts of diagnostic reagent as compared to other known recombinant peptides. Other advantages of the peptide are related to the size of the antigenic segment. The segment has improved stability as compared to larger antigenic segments and contains fewer noncritical antigens which minimizes the possibility of "false positive" results when employed as a diagnostic reagent to detect HIV infections. It is believed that noncritical antigens also illicit detrimental antibodies in non-infected individuals when administered as a vaccine.

Since the peptide is produced by recombinant DNA technology, it has several advantages over more traditional vaccine approaches using killed or attenuated viral preparations. Recombinant peptides are safe to prepare and administer. Since the peptide is administered, no genetic information is introduced by vaccination. In addition recombinant peptides are more readily produced and purified than native peptides isolated from virus infected cells.

In one embodiment, the peptide of the invention is used in a diagnostic kit used for detecting antibodies to HIV in a biological sample. The peptide can be employed in a process for detecting antibodies to HIV comprising contacting a biological sample with the peptide and detecting immunoreactivity. The peptide can also be employed as a component in a vaccine protective against HIV. The vaccine comprises an effectively protective amount of the peptide linked to a substantially antigenically neutral carrier.

In a preferred embodiment, the peptide comprises an antigenic segment having an amino acid sequence which corresponds to that encoded by the BglII to BamH1 nucleotide sequence of HIV shown in FIG. 2, and most preferably, an amino acid sequence which corresponds to that encoded by the BglII to HindIII nucleotide sequence of HIV also shown in FIG. 2. In another preferred embodiment, the peptide has about 340 amino acids which correspond to 54 amino acids from the N-terminal of the poliovirus sequence of pEXC, 46 amino acids of the C-terminal of the gp120 domain and about 240 amino acids of the N-terminal of the gp41 domain as shown in FIG. 4. This peptide is defined hereinafter as ENV9.

The peptide of the invention can be obtained by the following procedure. The DNA of a HIV clone, c-DNA of HIV, a DNA sequence corresponding to that of HIV, or a fragment thereof, preferably derived from HIV clone λBH10, is digested to obtain a nucleotide sequence encoding the desired amino acid residues. As used herein, the expression "nucleotide sequence" refers to a polymer of DNA or RNA which can be single- or double-stranded, optionally containing synthetic, non-natural, or altered nucleotides capable of incorporation into DNA or RNA polymers. The specific restriction endonuclease or combination thereof which is employed to generate the desired nucleotide sequence is not critical. Preferably, restriction enzymes BglII and BamH1 are employed to obtain the nucleotide sequence from base pair 7198 to base pair 8052 (FIG. 2), and most preferably, restriction enzymes BglII and HindIII are employed to obtain the nucleotide sequence from base pair 7198 to base pair 7721 (FIG. 2).

The nucleotide sequence is ligated into a vector which is employed to transform a host microorganism strain, preferably a bacterial strain, and most preferably *E. coli.* The term "vector" refers to a DNA molecule which contains, inter alia, genetic information to insure its own replication when transformed into a host microorganism strain. Examples of vectors commonly used in bacterial genetics are plasmids and the DNA of certain bacteriophages. The particular vector which is employed to transform a selected host microorganism strain is not critical. In a preferred embodiment, the BglII/BamH1 nucleotide sequence described above is ligated into BglII/BamH1 cleaved DNA of an expression vector, preferably the poliovirus protease expression vector pEXC or a derivative thereof. The expression vector pEXC is depicted in FIG. 3 and described by Ivanoff et al., PNAS, 83:5392–5396 (1986) (hereinafter Ivanoff et al.), the disclosure of which is incorporated herein by reference.

The transformed cells are grown and harvested to yield the peptide of the invention. Transformants are selected, preferably by use of a colony hybridization technique using a nick translated 32labeled probe obtained from the env region of BH-10.

*E. coli* strain MM294 transformed with plasmid pENV9 encoding ENV9 and described in Example 1, has been deposited with the American Type Culture Collection (ATCC), Rockville, Md., and bears deposit accession No. ATCC67308. This deposit is available to the public upon the grant of a patent to the assignee. However, it should be understood that the availability of a deposit does not constitute a license to practice the subject matter in derogation of patent rights granted by governmental action. The preferred peptide defined herein as ENV9 can be isolated from plasmid pENV9 with restriction endonucleases BglII and BamH1 as described in Example 3.

Methods for digesting, identifying, recovering and purifying the various nucleotide sequences which encode the peptide of the invention are known to those skilled in the art as are methods for ligating the sequences into vectors, transforming host microorganism strains, cloning and recovering products synthesized. Accordingly, the methods will only be described by reference to specific embodiments of the invention set forth hereinafter.

Materials and Methods

Unless otherwise specified, parts and percentages are by weight and degrees are Celsius.

Strains and Plasmids

*E. coli* MM294 (F-, endA1, hsdR17, supE44, thi-1, λ-, restriction-negative, modification-positive), HB101 (F-, hsdS20, supE44, ara-14, galK-2, lacY1, proA2, rspL20 (str), xyl-5, mtl-1, λ-, recA1 gyrA96) were used as the host strains. The plasmid employed was derived from the pKGP36.trp previously described by Ivanoff et al., which contains the tryptophan (trp) promoter-operator and Shine-Dalgarno sequences from pLD102(20) inserted into the ClaI site of pBR322. The plasmid, pEXC previously described by Ivanoff et al., contains a cDNA segment encoding for the poliovirus 3C protease placed under trp control. The pEXC derivative employed in the Examples maintains the original PvuII site within the pBR322 sequence and thus contains a single BglII site.

Immunoblot Analysis

*E. coli* cells harboring the plasmid constructions were grown in minimal media (supplemented with 100 μg/ml ampicillin):n to induce expression from the trp promoter according to the procedure described by Nichols et al., *Methods in Enzymology*, 101:155 (1983). The cells were grown for about 18 hours and a 1/20 dilution of the resulting culture was made using the minimal medium. After 6 hours at 37°, 1 mL of the cells were centrifuged and the resulting pellet was dissolved in 1×SGB (2.0% SDS, 0.1M Tris (pH 6.85), 7.5% glycerol, 0.14 BME). Samples were boiled for 5 minutes and subjected to SDS/polyacrylamide gel electrophoresis. The resulting proteins were transferred to nitrocellulose filters by standard procedures described by Towbin et al., *PNAS*, 76:4350 (1979).

The panel of AIDS patient sera used in the Examples was provided by A. Bodner (Biotech Research Laboratory, Rockville, Md.) and T. Matthews (Duke University. Durham, NC). The filters were incubated with Blotto as described in Johnson et al., *Gene Anal. Tech.*, 1:3–8 (1984) for 1 hr at ambient temperature, then washed with phosphate-buffered saline containing 05% Tween 20 (PBS-T) for 1 hr. Patient sera (1:50 dilution in Blotto plus normal goat serum) was added to the filter and incubated overnight at 4° C. The filter was then rinsed with PBS-T (4×, 10 min.) and treated with the horseradish peroxidase-conjugated anti-human IgG (Vector Laboratories) or the biotin-avidin system (Vector Laboratories).

Enzyme Linked Immunosorbant Assay (ELISA)

Purified protein was diluted in 60mM carbonate pH 9.6 buffer containing 0.01% azide and 0.00006% SDS to obtain a protein concentration of 20 ng/well. 100 μL aliquots of the protein solution were placed in each well of Immulon II microtiter plates. The volume used in the binding step set the total volume used for all the rest of the incubations with the exception of the blocking steps. Binding took place at 4° for about 18 hours. The plates were then washed with PBS +0.05% Tween 20 (PBS-T). Plate washings were performed using 2–3 cycles on a Titertek Microplate Washer 120 followed by rotating the plate and washing again. The plates were blocked with PBST for 1 hour at 37° and were then washed 3X with PBS-T and stored dry at 4° until they were used.

The plates were reacted with patient sera at a 1:20 dilution in diluent (PBST +5% bovine serum albumin 20% heat inactivated NGS and 0.1% sodium azide with 0.05% thimerosal) in the microtiter wells and incubating for 2 hours at 25°. The plates were then washed with PBS-T, exposed to goat anti human IgG linked to alkaline phosphatase for 1 hour at 25° and washed with PBS-T. The color was developed by exposure to 72 μg para-nitrophenylphosphate in 100 1 of diethanolamine buffer (IM) with magnesium chloride and 0.02% sodium azide at a pH of 9.8 for 30 minutes at 37° followed by addition of sodium hydroxide to a concentration of 1N. The plates were read on a Titertek Multiskan MCC microtiter plate reader at a wavelength of 405 nm.

EXAMPLES

The invention is further described by the following Examples, wherein all parts and percentages are by weight and degrees are Celsius.

EXAMPLE 1

Construction of Plasmid pENV9

The plasmid pENV9 was constructed by combining the BglII/BamHI env fragment (n7196-8053) with the BglII/BamHI vector fragment of pEXC. The unique in-frame BglII site within the poliovirus protease coding sequence of the pEXC vector was utilized to create this protease/env fusion.

Restriction endonucleases, T4 DNA ligase, T4 polynucleotide kinase, and the Klenow Fragment of DNA polymerase I were obtained from New England Biolabs or Bethesda Research Laboratories, and used as recommended. About 5 μg of DNA (pEXC or BH10) were digested with the restriction endonucleases Bgl II and BamH I (10-20 units) in a buffer containing 6.6 mM TRIS, pH 7.6; 6.6 mM MgCl$_2$; 6.6 mM dtt; and 50mM NaCl for 2 hours at 37°. The resulting DNA fragments were separated by agarose electrophoresis (1% agarose gel in 0.04M Tris-acetate and 0.002M EDTA buffer) according to the procedure set forth in Maniatis et al., *Molecular Cloning*, a Laboratory Manual (Cold Springs Harbor Laboratories, Cold Spring Harbor, N.Y., 1982) (hereinafter Maniatis et al.). The DNA fragments were purified by high salt elution from DEAE-cellulose strips (Schleicher & Schuell).

The fragments of interest were electrophoresized onto DEAE-cellulose strips, which were then incubated in a buffer containing 1M NaCl, 20 mM Tris (pH 8), 0.1 mM EDTA for three hours at 65°, in order to elute the DNA fragments. The purified 4150 base pair vector pEXC fragment (200ng) and the 850 base pair env fragment (200 ng) were ligated using T4 DNA ligase (400 units) in a buffer containing 50 mM Tris (pH 7.8), 10 mM MgCl$_2$, and 20 mM dtt for 12 hours at 12°. A 10 μL aliquot of the resulting ligation reaction mixture was used to transform E. coli strain HB101 and MM294 by the procedure described by described by Hanahan, J. Mol. Bio., 166:557–580 (1983).

The resulting transformants were screened by colony hybridization using an env specific probe. The probe was a M13 phage subclone of the env region which was radiolabeled with $^{32}$P dATP in a polymerization reaction (2 mM dNTPs, 10 mM Tris-HCl. (pH 7.5), 5mM MgCl$_2$, dtt, 25 units of Klenow fragment) for 2 hours at 4°. The *E. coli* transformants were transferred to nitrocellulose filters and then lysed (cells disrupted and DNA exposed) by the following procedure: 0.2 M NaOH, 1.5 M NaCl for 5 minutes; 1.4 M Tris, 1.5 M NaCl for 5 minutes; 0.36 M NaCl 0.02 M NaH$_2$PO$_4$ (pH 7.4), 2 mM EDTA for 5 minutes. The resulting filter were baked at 80° for 2 hours then placed in a plastic bag and mixed with the radioactive probe described above (10$^{-6}$ cpm/filter). The filters were hybridized at 25 ° for 12 hours in a buffer containing 0.18M NaCl, 0.01M NaH$_2$PO$_4$ (pH 7.4) and 1 mM EDTA. The filters were then washed with fresh buffer and then placed at 40° for 4 minutes.

The resulting clones that hybridized strongly with the probe were selected and analyzed for DNA by the alkali lysis procedure described by Maniatis et al. The presence of the plasmid construction pENV9 was verified by restriction analysis. The predicted protein product of the resulting plasmid (ENV9) contains about 340 amino acids which correspond to about 54 amino acids from the N-terminal of the poliovirus sequence of pEXC, about 46 amino acids of the C-terminal of the gp120 domain and about 240 amino acids of the N-terminal of the gp41 domain.

EXAMPLE 2

Reactivity of ENV9 with Virus Specific Antibodies

Monoclonal antibodies raised to gp41 viral protein and gp120 viral protein were found to react specifically with ENV9 when tested in immunoblot and ELISA according to methods described previously. The monoclonal antibody raised to gp120 viral protein employed in this example is commercially available from New England Nuclear, E. I. duPont de Nemours and Company, Medical Products Department under Catalog No. NEA 9284. These results confirm that viral antigenic sites reside within ENV9. In addition, antibodies to a synthetic peptide encoded by the last 16 amino acid residues of the C-terminal of gp120 were found to react specifically with ENV9 in immunoblot and ELISA.

EXAMPLE 3

Purification of Recombinant Peptide ENV9

The peptide ENV9 was purified from the *E. coli* cells containing the vector pENV9 described in Example 9 according to the following procedure. The *E. coli* were grown in a rich medium lacking tryptophane and the resulting culture was centrifuged. The resulting pellet was resuspended in dilute buffer and sonicated. After centrifugation, the lysed cell pellet was extracted with 80% acetic acid. The extracted material was then subjected to large scale reverse phase chromatography in the presence of acetonitrile and 1% trifluoroacetic acid. The immunoreactive material eluted from the column was lyophilized and later reconstituted in 10% SDS in phosphate buffer saline (PBS). The ratio of protein to SDS was kept at 2. The solubilized protein was then subjected to size exclusion chromatography using Superose TM 6 in the presence of PBS +0.1% SDS. Protein from this column was identified by its immunoreactivity and was visualized by coomassie blue staining in polyacrylamide gels.

EXAMPLE 4

Use of ENV9 as an Immunogen

Another advantage of the antigenic structure of ENV9 is the peptide's ability to illicit virus specific antibodies in animals. Purified ENV9 was injected into rabbits, goats, and mice and the resulting antisera was assayed by immunoblot and ELISA according to the methods described previously. Goat and rabbit antisera to ENV9 reacted with the expected viral envelope proteins gp41 and gp120 on viral immunoblot. Antisera to ENV9 also reacted with HIV ELISA.

It was found that goat antisera to ENV9 was capable of precipitating purified viral gp120. The strength of the antisera was found to be equal to or greater than goat antisera to natural gp120 in recognizing and precipitating the viral gp120 protein. This result demonstrates that ENV9 contains a major native viral epitope and that antibodies to ENV9 are sensitive reagents for detecting viral proteins.

EXAMPLE 5

Immunoreactivity of ENV9

Purified ENV9 was employed to detect antibodies to HIV in AIDS patient sera. The reactivity of HIV positive sera at a dilution of 1:500 gave results above background at a concentration of antigen of 20 ng/well for the peptide. Using this concentration, four HIV positive sera and an equal number of negative sera were tested at dilutions ranging from 1:100 to 1:1600. The absorbance was directly proportional to the amount of serum. The reactivity of the negative sera were quite low for the ELISAs. The results of testing 330 negative and 53 positive samples with the assay described above are shown in Table 1.

TABLE 1

Frequency distribution of Seropositive and Seronegative Individuals with ENV-9 ELISA

| ELISA Assay | Status | Number of Individuals in Each Absorbance Range: 0-0.2 | 0.2-0.4 | 0.4-0.6 | 0.6-0.8 | 0.8-1.0 | 1.0-2.0 | >2.0 |
|---|---|---|---|---|---|---|---|---|
| ENV-9 | Positive | 0 | 0 | 0 | 0 | 0 | 5 | 48 |
| | Negative | 319 | 9 | 0 | 1 | 2 | 0 | 0 |

The seropositive samples used in this study were diagnosed AIDS patients. These were confirmed by other ELISA assays as well as by immunoblot samples run at a dilution of

What is claimed is:

1. A recumbinant peptide displaying the antigenicity of Human Immunodeficiency Virus (HIV) viral antigens comprising an antigenic segment having about 286 amino acids corresponding to about 46 amino acids of the C-terminal region of the gp120 domain and about 240 amino acids of the N-terminal region of the gp41 domain, said antigenic segment corresponding to the amino acid sequence shown in FIG. 2.

2. A peptide as defined in claim 1, wherein the antigenic segment has an amino acid sequence which corresponds to that encoded by the BgIII to BamH1 nucleatide sequence of HIv shown in FIG.2.

3. A peptide as defined in claim 1, wherein the peptide contains about 340 amino acids which correspond to about 54 amino acids from the N-terminal region of the poliovirus sequence of pEXC, about 46 amino acids of the C-terminal region of the gp120 domain and about 240 amino acids of the N-terminal region of the gp41 domain, as shown in FIG. 4.

4. In a diagnostic kit comprising a collection of materials containing all major components used for detecting antibodies to HIV in a biological sample and comprising a container containing an HIV antigen, and means for detecting an immune reaction of HIV antibodies with said HIV antigen, the improvement wherein the HIV antigen comprises a peptide of claim 1.

5. In a diagnostic kit comprising a collection of materials containing all major components used for detecting antibodies to HIV in a biological sample and comprising a container containing an HIV antigen, and means for detecting an immune reaction of HIV antibodies with said HIV antigen, the improvement wherein the HIV antigen comprises a peptide of claim 2.

6. In a diagnostic kit comprising a collection of materials containing all major components used for detecting antibodies to HIV in a biological sample and comprising a container containing an HIV antigen, and means for detecting an immune reaction of HIV antibodies with said HIV antigen, the improvement wherein the HIV antigen comprises a peptide of claim 3.

7. In a method for detecting antibodies to HIV in a biological sample wherein the biological sample is contacted with an HIV antigen and immunoreactivity is detected, the improvement comprising contacting the biological sample with a peptide of claim 1.

8. In a method for detecting an antibodies to HIV in a biological sample wherein the biological sample is contacted with an HIV antigen and immunoreactivity is detected, the improvement comprising contacting the biological sample with a peptide of claim 2.

9. In a process for detecting antibodies to HIV in a biological sample comprising contacting said sample with a peptide which is immunoreactive with said antibodies and detecting immunoreactivity, the improvement comprising employing the peptide of claim 3.

* * * * *